US010751202B2

(12) United States Patent
Joseph

(10) Patent No.: US 10,751,202 B2
(45) Date of Patent: Aug. 25, 2020

(54) PROSTHETIC LIMB SOCKETS AND METHODS OF MAKING AND USING

(71) Applicant: MEDICAL CREATIONS, INC., Aspen, CO (US)

(72) Inventor: Mark Joseph, Aspen, CO (US)

(73) Assignee: MEDICAL CREATIONS, INC., Aspen, CO (US)

( * ) Notice: Subject to any disclaimer, the term of this patent is extended or adjusted under 35 U.S.C. 154(b) by 127 days.

(21) Appl. No.: 15/914,480

(22) Filed: Mar. 7, 2018

(65) Prior Publication Data

US 2019/0274850 A1 Sep. 12, 2019

(51) Int. Cl.
A61F 2/78 (2006.01)
A61F 2/80 (2006.01)
A61F 2/50 (2006.01)
A61F 2/76 (2006.01)

(52) U.S. Cl.
CPC .............. A61F 2/80 (2013.01); A61F 2/5046 (2013.01); A61F 2/76 (2013.01); A61F 2002/5052 (2013.01)

(58) Field of Classification Search
CPC .. A61F 2/76; A61F 2/80; A61F 2/5046; A61F 2002/5052
See application file for complete search history.

(56) References Cited

U.S. PATENT DOCUMENTS

| | | | |
|---|---|---|---|
| 4,019,505 A | 4/1977 | Wartman | |
| 4,704,129 A | 11/1987 | Massey | |
| 5,376,127 A | 12/1994 | Swanson | |
| 5,824,111 A | 10/1998 | Schall et al. | |
| 5,885,509 A * | 3/1999 | Kristinsson | A61F 2/5046 264/314 |
| 5,980,803 A | 11/1999 | Slemker et al. | |
| 6,444,282 B1 | 9/2002 | Shirer | |
| 6,869,560 B1 | 3/2005 | Drouin et al. | |
| 8,303,527 B2 | 11/2012 | Joseph | |
| 2008/0269914 A1 | 10/2008 | Coppens et al. | |
| 2014/0025183 A1 | 1/2014 | Kelley et al. | |
| 2016/0143752 A1 | 5/2016 | Hurley et al. | |

FOREIGN PATENT DOCUMENTS

WO WO 2014/182537 A1 11/2014

OTHER PUBLICATIONS

Bracken, S., "Graduate student works to make prosthetics accessible in developing countries," PennState News, Feb. 2, 2016, 5 pages, [Online] [Retrieved on Aug. 20, 2019],<URL: https://news.psu.edu/story/390530/2016/02/02/academics/graduate-student-works-make-prosthetics-accessible-developing>.

(Continued)

Primary Examiner — Bruce E Snow
(74) Attorney, Agent, or Firm — Aspire IP; Scott J. Hawranek

(57) ABSTRACT

The present disclosure is directed to prosthetic limb sockets that couple prosthetic limbs to residual limbs. The sockets include a conical cup sized to engage and couple to the residual limb, and a base to secure the socket to the prosthetic limb. The sockets are direct heat-formable onto the residual limb, such that they can be heated and formed as they are secured to the residual limb.

20 Claims, 14 Drawing Sheets

(56) References Cited

OTHER PUBLICATIONS

Dupere, K., "The 12 most impressive social good innovations from June," Mashable, Jul. 1, 2016, 10 pages, [Online] [Retrieved on Aug. 20, 2019],<URL: https://mashable.com/2016/07/01/social-good-innovations-june-2016>.
Kemp, T.., "Affordable, Adjustable Socket in the Works for Amputees in Need," O&P News, Jun. 1, 2016, 5 pages, [Online] [Retrieved on Aug. 20, 2019] <URL: http://oandpnews.org/2016/06/01/affordable-adjustable-socket-in-the-works-for-amputees-in-need/>.
U.S. Appl. No. 61/820,233, filed May 7, 2013, Inventors: Zhe et al. [copy not enclosed].
Wilson Jr., A. B., "A Material for Direct Forming of Prosthetic Sockets," Artificial Limbs, Spring 1970, pp. 53-56, vol. 14, No. 1.
PCT International Search Report and Written Opinion, PCT Application No. PCT/US2019/020484, Jun. 7, 2019, 12 pages.

\* cited by examiner

PROSTHETIC LIMB SOCKETS AND METHODS OF MAKING AND USING

FIELD

The present disclosure generally relates to sockets for prosthetic limbs, and more specifically, to prosthetic sockets having improved conformability to residual limbs.

BACKGROUND

A prosthetic socket for amputated limbs typically fits precisely and tightly to the residual limb to bear the weight of a patient previously placed on the now-missing limb, spreading the force from amputated bone ends and bone prominences and to soft portions of the residual limb. Fitting prosthetic sockets to residual limbs is carried out by an experienced prosthetist (as a prosthetic practitioner is called), and typically requires a high degree of training and experience. The typical process for making such sockets requires casting of the residual limb by wrapping with casting plaster (similar to making a fracture cast) to make a negative form, then filling the form with plaster to make a precise positive model of the residual limb.

The prosthetist must carefully evaluate the residual limb, alignment, stance and sensitivities, and determine the desired load bearing characteristics of the socket. Typically, to achieve a proper tight fit, the entire model must be reduced in circumference to some degree. In some areas, the model may be increased or material added to create pockets that reduce contact with sensitive areas of the residual limb. Using abrasive files, sand paper, and scraping tools, the prosthetist adjusts the diameter and shape of the model by hand, in an imprecise manner, to approximate the shape that is presumed to be appropriate for the intended outcome. Some prosthetists use computer scanning and manipulation to achieve this, but the process is still experience based and imprecise.

Once the model shaping process is complete, the socket is created by heating high temperature thermoplastics and forming them over the model using complicated and time-consuming techniques. Typically, over half of the materials required become scrap and must be disposed of. In many cases, the socket is made from fiberglass and toxic two-part resin. The resin must be cured, and forms a very rigid socket that can only be modified by grinding away material. These sockets are finished on the edges and surfaces using time-consuming and messy methods, and are then test fitted to the residual limb. Because the model shaping process is imprecise and based on estimation, often several time-consuming adjustments must be made to the socket for proper fitment, requiring several visits to the prosthetist and time consuming techniques to make adjustments.

This entire complicated process requires a large workshop with expensive machinery, ventilation, and extensive materials inventory, making it impractical to produce sockets in hospitals or off site. Many prosthetists perform only the initial casting and final fitting procedures because they do not have a sufficient workshop, and must send away to a socket making service further complicating the process and adding cost. Often, it is determined that the socket was improperly made and the entire process must be started again.

In the case of recent amputees, the residual limb is very sensitive, and over the period of months, can atrophy and shrink substantially, change shape, and develop callus. During this time, temporary "test" sockets are made using the above process, yet frequently with less durable materials because the sockets may only be worn for a short period until a subsequent one, started from scratch, is needed. This process may be repeated from three to five times depending on the amputation and amputee conditions, thereby significantly increasing the time, effort, waste, office visits, travel and efforts required of all involved.

This process is very stressful for the amputee. It is painful, time consuming, and often requires distant travel. It can take hours and days of waiting for adjustments to be made. The amputee typically must make several trips to the prosthetist and wait days or weeks for the socket to be completed. The process of making adjustment is limited, and therefore the entire process must be repeated if the prosthetist is unable to adjust the socket enough to achieve the desired results. Then, the amputee must get used to wearing the new socket which can involve weeks of pain, the final outcome being unknown until comfort is achieved.

Cost is another serious consideration. Insurance, which may covers prosthetics, can be extremely limited, and may not pay for another prosthetic for years, even if the current one is working poorly. For the prosthetist, insurance reimbursement is often a one-time fee based on the amputation and equipment approved. The number of times the prosthetic must be made and adjusted is not reimbursed for, and therefore the prosthetist loses profit every time the patient returns. The process is so difficult that amputees often put up with less than desirable fit, chronic pain, and use/walking challenges for months or even years before going through the process again.

In order to improve upon the challenges of making a socket in the conventional manner previously described, attempts have been made in the past to direct mold low temperature thermoplastic sockets onto residual limbs. These methods have not been widely accepted or used by prosthetists. Low temperature thermoplastic materials, such as polycaprolactone, have been used. Such materials are formable at between 120° F. and 180° F. (50° C. to 80° C.). They are typically heated in hot water and can be applied directly to the skin. These materials have inadequate strength and rigidity to hold up to the rigors of weight bearing and the abuse of walking. They also tend to become very difficult to work with because when heated they become clay like, extremely sticky and are very difficult to form tightly to the limb. Therefore, the sockets produced using these materials are inadequate and undesirable. While these sockets may occasionally be used as temporary sockets, they are typically not used as permanent sockets.

Other currently-used sockets have a hard supportive outer shell made in the typical fashion, and a softer, low temperature direct on-body heat-formed inner liner. While these sockets can perform adequately, they still require the same time-consuming steps needed to make the outer socket which is rigid, made of high temperature thermoplastics or fiberglass, and must be custom made using casting and a model as described above. Additional steps are required to mold the inner soft non-supportive liner using a heat forming direct-on-body process. If the outer hard socket is not properly formed and fitted, the inner soft liner may not adequately adjust to the residual limb.

Readily available low temperature thermoplastics used in the above-described methods are typically polycaprolactone or derivatives. This is because the plastics industry only recently developed thermoplastics that can be readily thermoformed at temperatures between 200° F. and 300° F. (between about 93° C. and 150° C.), and which have adequate physical properties. Temperatures above 300° F.

are impractical because the residual limb would be burned by such hot materials applied to the body, even with an insulative liner. It should be noted that the physical properties for a prosthetic socket regarding durability, elongation, crack resistance and rigidity until recently were only achieved with materials thermoformed over 350° F. (about 176° C.) or with fiberglass and/or carbon fiber impregnated with resin.

The previously described methods of directly heat forming sockets to residual limbs have been largely unsuccessful and, as a result, are not prevalent in the market.

SUMMARY

The present disclosure describes prosthetic sockets for amputated limbs that are formed directly to the residual limb of the patient using proprietary materials that are dry-heated to become pliable and stretchable. This eliminates casting the residual limb along with the model making process, and drastically reduces the number of steps required to make a socket. Direct forming also reduces the imprecise hand grinding and shaping method currently used to adjust the model, in addition to forming the final high temperature plastic or fiberglass/resin socket to the model. Sockets in accordance with the present disclosure utilize the residual limb to form the socket and create a precise, tight fit. The present disclosure describes original features, materials and methods that will allow prosthetists to quickly and efficiently direct-heat form a prosthetic socket to the residual limb which has a precise tight fit, is durable, light weight, re-formable, and saves time, materials, and cost.

Sockets in accordance with the present disclosure are formed from proprietary thermoplastic materials which allow the sockets to be heat formed at higher temperatures than previously used. A prosthetic liner sufficiently thick and insulative to protect the residual limb from the higher temperatures is worn on the limb during forming of the socket. Amputees commonly wear such liners to protect the residual limb and hold the socket firmly to it. They can, for example, comprise stretchable gel with an outer stretch fabric lining. The gel may comprise silicone, polyurethane or other similar materials that are compatible with the skin and, using circumferential tightness, will hold firmly to the limb. Various attachment member may be used to hold the liner to the socket, and sockets in accordance with the present disclosure may be compatible with such attachment member. Other suitable insulation types may include fabric liners comprising cotton, various foams, and other materials that are sufficiently insulative.

Thermoplastic materials that form at higher temperatures can be engineered chemically to have improved physical properties over those used in previous lower temperature methods, such as those methods as previously described herein. Leg prosthetics, for example, are subjected to many thousands of steps, high body weight, running, jumping and other actions, which exert considerable force on the socket and to its attachment to the replacement leg prosthetic. Arm prosthetics, while not bearing weight, can also require very strong construction. A viable socket must have excellent properties of rigidity, elongation, impact resistance, crack propagation and creep in order to be durable enough for these rigors. Polymer science now provides plastics that can be heat formed at temperatures well above previous attempts, yet below those used for conventional prosthetic sockets.

The present disclosure describes methods of making sockets using thermoplastics that become malleable, stretchable, and formable at higher temperature ranges, such as, for example, between about 225° F. and 275° F. (between 107° C. and 135° C.) (the target heat range). This temperature range is novel and ideal because it is the highest range that can be comfortably and safely formed over the residual limb with an insulating gel liner as previously described. It is also a considerably higher temperature than previous attempts have used and therefore, the thermoplastic can have adequate properties of rigidity, elongation, impact resistance, crack propagation and creep in order to be adequately durable. Various additives can be incorporated into the higher temperature thermoplastic to improve strength including but not limited to carbon fiber, aramid fiber, fiberglass, glass micro, carbon nanotubes beads, and others.

Sockets in accordance with the present disclosure are formed by injection molding. A number of suitable sizes and shapes are provided which correspond to the various common residual limb sizes. When a socket is sized by the prosthetist, it will be smaller in circumference than the residual limb so that it can be stretched on for a tight fit. In various embodiments, sockets may be injection molded of a single polymer type, or a secondary over molding process can be used to co-join two different polymers to provide varied featured in various places. For example, the upper portion of a socket can be made of a polymer that becomes more formable in the target temperature range so that it can be easily formed to the limb details.

In various embodiments, a lower portion of a socket comprises a polymer that is less formable than the upper portion in the target heat range. This lower portion can, when heated, provide a more supportive area for a socket base as the upper portion is stretched over the limb, and the limb is forced down into the socket. However, it can also conform to the residual limb to some degree. The lower portion can also be a material that has a higher forming temperature and thus can have even greater physical properties to accommodate the higher forces applied to the base of the socket and the attachment to the prosthetic. The lower portion is also required to hold its shape when heated so that the connections to the prosthetic, and other critical features, do not deform during the heating and forming processes. Additionally, the socket can comprise a third polymer section at the base that does not become malleable at the target temperature range in order to hold its features precisely during heating and forming. This portion may be over molded as well, or attached by fasteners to the upper socket section.

In various embodiments, complex and detailed features can be molded into the socket to achieve various effects by, for example, injection molding. The polymer materials can be varied in either composition or thickness to precisely provide increased support or more formability as desired. Three dimensional elements can be used to provide support and strength such as ribbing, tapered sections, corrugations, cross hatched reinforcements and the like. For below-the-knee amputations, for instance, areas near the end of the tibia and fibula can require extra care in forming so that the socket provides extra room in these areas. These areas could be made thinner and thus easier to expand and form. Adjacent areas could have ribbing to provide more support and strength.

Once the socket is formed to the amputee, the top must be trimmed and smoothly finished. This can be efficiently performed by heating the top portion with a heat gun and using shears to cut the top to the preferred height and shape. A hand rotary electric grinder can be used to smooth the top edge. Spot heat can be applied to adjust the top edge, to flair portions and tighten others to the limb. These tools can be portable and may produce only a small amount of grit and dust that can be easily contained and cleaned up.

At any time, due to the low temperature formability of the polymer, a forced air heat gun can be used to spot heat the socket, often while the socket is worn by the amputee. Pressure can be applied and adjustments quickly made in a precise manner. Additionally, if the socket shape proves dysfunctional, the entire socket can be re-heated and reformed quickly and precisely. This can prove especially valuable in the case of atrophy or changes to the muscles over time. Rather than starting the typical process over again by discarding the socket and casting a new one, this reheating and reforming process saves a great deal of time, materials and expense. The time required to form and finish a socket of the present disclosure may, for example, be under two hours, and can be completed in one sitting. Compare this to the many hours, steps, drying and curing time, finishing and adjusting time required for the typical socket, which can take days or weeks. The benefits to the prosthetist and amputee are considerable.

The typical process of making a socket requires a great deal of attention be paid to the base of the socket where the locking mechanism for the socket connects to the gel liner. Also, the metal connection to the leg or arm extension must be built into the base in a strong manner. Typically, a large inventory of the various locking mechanisms and attachment parts must be maintained to meet the various needs of the prosthetic. The prosthetist hand builds these devices into the base of the socket requiring a great deal of skill, knowledge and time. In various embodiments, injection molding of a socket permits the addition of elements or physical features into the socket, such as the base, adjustment, and locking mechanisms. For example, elements used by a locking mechanism of a prosthetic can be modular, interchangeable, and insert quickly into the base of the socket so the prosthetist can simply pick the type of locking mechanism and attach any number of connectors for the leg extension in minutes.

The precision injection molding process can also allow the base of the socket to include adjustment mechanisms for attaching the prosthetic. Often, the prosthetic must be offset horizontally from the center of the bottom of the socket in order to properly align the socket for optimal use, gait, and balance. Sockets can, for example, include an attachment member for the prosthetic that uses the common four flat head bolts typically used to attach the metal base plate. This baseplate attaches in an angularly adjustable manner to the prosthetic. By loosening the four bolts, the base plate can be slid and adjusted in a planar horizontal manner to offset the prosthetic as desired. Tightening the four bolts locks it in place. This feature complements the easy adjustability of the heat formable socket by providing instant alignment to save the amputee and prosthetist time, materials and cost. Additionally, angular adjustment can be achieved by a ball and socket type of connection to the lower base that can be loosened, rotated, and tightened.

Methods of the forming sockets of the present disclosure may significantly reduce the equipment required to fit and finish a socket. For example, a heating bag, less than 2'×1'×6" is simply plugged in and can be safely handled due to its insulated nature. Further, a hand-held heat gun is small, inexpensive and portable. The tools required by the methods of the present disclosure can include gloves, elastic straps, vacuum bags and the like, which are relatively small and portable. The equipment required to cut and finish the top of the socket is again, hand held, plugged in and portable. All of the tools required to fit and finish the invention of the exemplary embodiment can be fitted into a suitcase making the system portable, non-toxic and relatively mess free. This allows for prosthetists in small offices, hospitals and clinics to fit and finish sockets themselves in under two hours. This system can also be mobile, so that prosthetists could make house and hospital calls to provide finished sockets. The potential in rural areas and developing countries is enormous.

Sockets made in accordance with the present disclosure my significantly improve the efficiency and outcome of making an amputee prosthetic socket, and allow for quick adjustment and reforming to achieve the best possible fit, comfort, and function.

Prosthetic limb sockets in accordance with the present disclosure can comprise a conical cup comprising a material having a first pliability at between about 160° F. and about 302° F. (between about 70° C. and about 150° C.) to be stretched circumferentially over a residual limb, a lower portion coupled to a lower surface of the conical cup creating an enclosed form having a second pliability which is less than the first pliability, and a base coupled to the lower portion, wherein the conical cup and the lower portion are injection molded of a thermoplastic polymer, wherein the conical cup and the lower portion, when heated to between about 160° F. and about 302° F. (between about 70° C. and about 150° C.) have a working time of between about five minutes and about 15 minutes before hardening as room temperature is approached, and wherein the conical cup and the lower portion each comprise a hardness exceeding ASTM D2240 of 50D shore hardness, a tensile strength exceeding ASTM D638 of 5,000 psi, and a flexural modulus exceeding ASTM D5023 of 150,000 PSI.

The conical cup and the lower portion can be unitary. Further, at least one of the conical cup and the lower portion can be injection molded, and the other of the conical cup and the lower is over-molded. The thermoplastic polymer of the conical cup can comprise at least one additive from the group of fiberglass, carbon fiber, aramid fiber, glass beads, and carbon nanotubes. The base can comprise a securing element.

The socket can further comprise an insert layer comprising one of a rubber, a polyurethane, an estane, spandex, a long chain polymer. The insert layer can be insert molded into the conical cup, and can cause the heated conical cup to become elastic and draw tight circumferentially over the residual limb as it is applied and formed. The socket can further comprise a thin outer layer surrounding at least a portion of the conical cup, and the outer layer can be co-molded or adhered to an external surface of the socket. Such an outer layer can provide body and support to the heated socket and be colored, printed, or decorated. The socket can further comprise an insulating layer attached to the residual limb and secured within the conical cup.

BRIEF DESCRIPTION OF THE DRAWINGS

The features and advantages of the present disclosure will become more apparent from the detailed description set forth below when taken in conjunction with the drawings, wherein.

DETAILED DESCRIPTION OF THE ILLUSTRATED EMBODIMENTS

Figure 1:
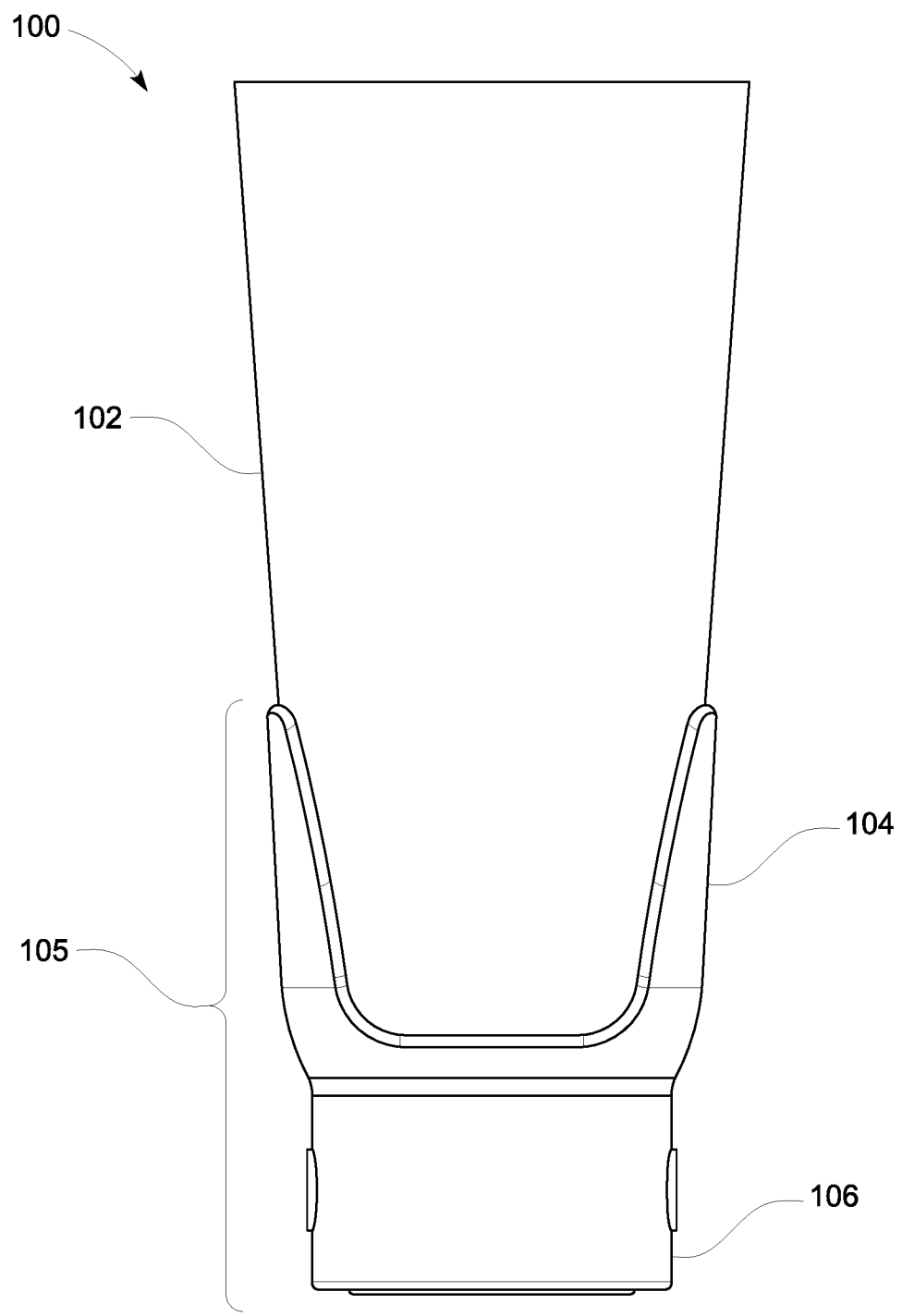
FIG. 1 illustrates a side view of a prosthetic limb socket in accordance with the present disclosure.

Persons skilled in the art will readily appreciate that various aspects of the present disclosure can be realized by any number of methods and articles configured to perform the intended functions. Stated differently, other methods and articles can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

Prosthetic limb sockets in accordance with the present disclosure are used to secure prosthetic limbs to the residual limb of a patient. In many cases, the prosthetist and patient selects an appropriate liner to apply to the residual limb. The liner reduces discomfort (such as chafing or rubbing) between the skin of the residual limb and a socket. The liner also has a very high friction interior that adheres to the skin to hold it in place during movement and has a connection means to the socket that can vary. The socket is applied over the liner, and acts to support and suspend a prosthetic limb to the residual limb of the patient. Stated another way, the liner is positioned between a residual limb and a socket, and the actual prosthetic limb is coupled to the socket.

In various embodiments, sockets comprise an upper portion and a lower portion. In certain embodiments, the upper portion has a first pliability in a given temperature range which is greater than the pliability of the lower portion in the same temperature range. The lower portion serves to support the socket during heat forming yet is still conformable when heated. The lower portion also has means to attach the prosthetic limb in an adjustable fashion and has attachment member for various mechanisms to lock the gel liner to the socket. In this case, the lowest portion that performs this function is not heated so it retains its shape and mechanical properties.

In yet other embodiments, the lower portion comprises a middle portion and a base, the base comprising a polymer that does not become malleable at all in the same temperature range that the upper portion and the middle portion become malleable. The upper portion interacts with and surrounds the residual limb (including, in most cases, a liner). The middle portion is co-molded to the upper portion and serves to support the socket during heat forming, yet is still conformable when heated, and is attached mechanically to the base. The base is adjustable in alignment and acts as an attachment portion for the prosthetic limb, coupling it to the socket (and in turn, to the residual limb of the patient). Sockets in accordance with the present disclosure comprise upper portions (referred to as conical cups) having improved flexibility, comfort, and/or engagement with the residual limb. In yet other embodiments, the socket is made of a single material that is pliable when heated, similar to the upper portion previously described. It is heated in a fashion so that the upper portion is heated more than the lower portion. In this manner, the upper portion will be more pliable, the middle portion will be moderately pliable and the base will remain rigid during the forming process so as to retain its mechanical shape and properties.

Figure 2:
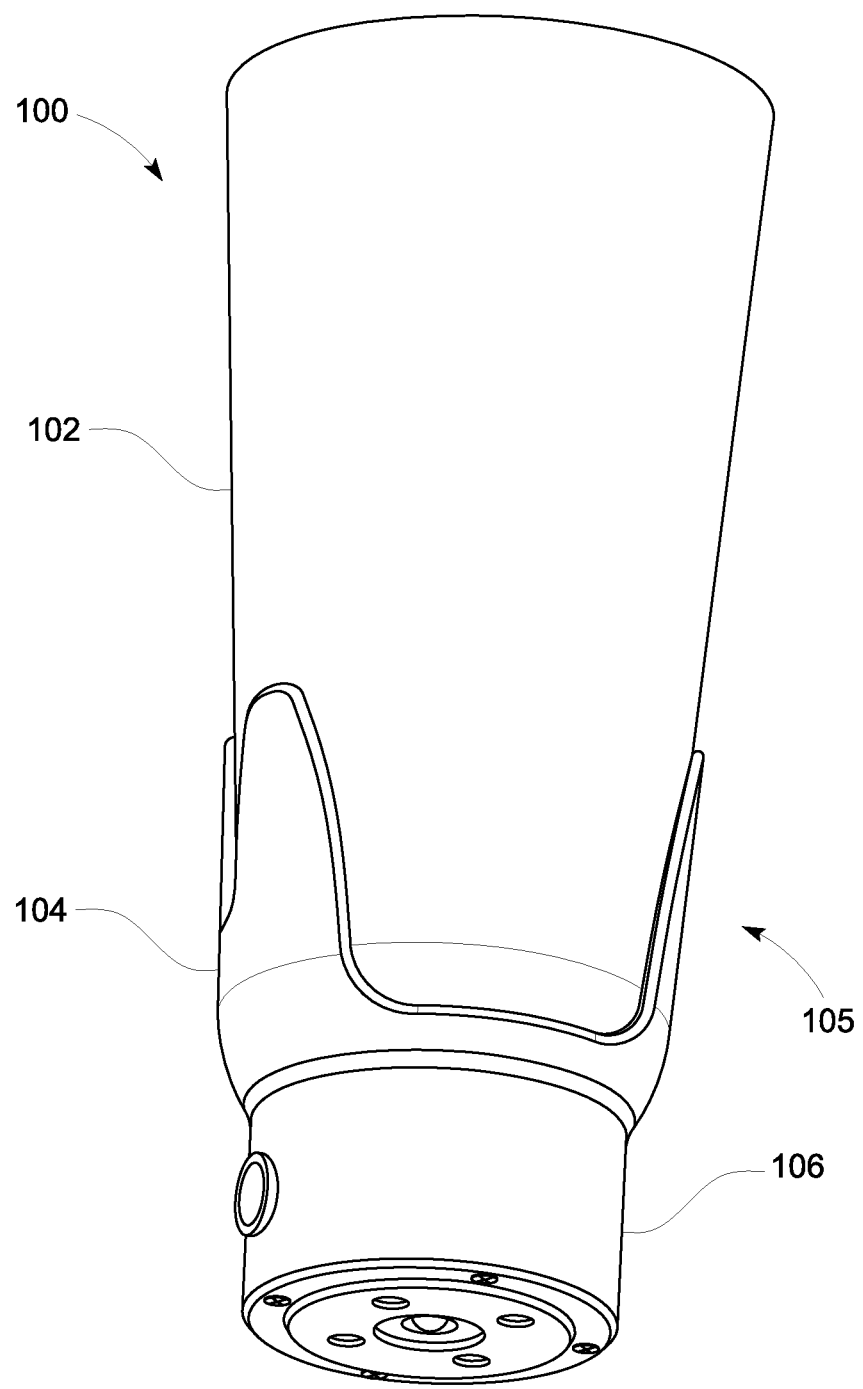
FIG. 2 illustrates a perspective view of the prosthetic limb socket of FIG. 1 in accordance with the present disclosure.

With initial reference to FIGS. 1 and 2, a prosthetic limb socket 100 in accordance with the present disclosure is illustrated. In various embodiments, the upper portion of socket 100 comprises a conical cup 102. Conical cup 102 is coupled to a lower portion 105.

Conical cup 102 is sized and configured to engage with a residual limb, securing socket 100 to the limb. Frequently, a liner is positioned around the outside of the residual limb. In such embodiments, conical cup 102 of socket 100 surrounds the liner. As noted, the liner may help reduce chafing and discomfort between the residual limb and conical cup 102, and secure them together. After conical cup 102 is positioned around and secured to the residual limb, a prosthetic limb can be attached to socket 100.

In various embodiments, conical cup 102 comprises a polymeric material. For example, conical cup 102 can be injection molded from a polymeric material. Conical cup 102 can, for example, comprise a polymeric material having a hardness exceeding ASTM D2240 of 70D shore hardness, a tensile strength exceeding ASTM D638 of 7,000 psi, and/or a flexural modulus exceeding ASTM D5023 of 250,000 PSI. Although described with reference to specific materials and methods of forming materials, any type of polymeric material and manner of making a suitable conical cup is within the scope of the present disclosure.

Conical cup 102 can further comprise, for example, a polymeric material having a pliability between about 160° F. and about 302° F. (between about 70° C. and about 150° C.), and further, between about 225° F. and about 275° F. (between about 107° C. and about 135° C.). In various embodiments, when heated to between about 160° F. and about 302° F. (between about 70° C. and 150° C.), the pliability of conical cup 102 provides a working time of between about five minutes and about 15 minutes before hardening. The pliability and working time allow conical cup 102 to be stretched circumferentially over the residual limb before conical cup 102 cools and re-hardens.

In various embodiments, conical cup 102 can comprise one or more additives which are added to the polymeric material to impart one or more desired physical and/or chemical properties to the polymeric material. For example, the polymeric material of conical cup 102 may comprise one or more of fiberglass, carbon fiber, aramid fiber, glass beads, carbon nanotubes, or other additives. Any additive that imparts or improves a desired physical or chemical property of the polymeric material of conical cup 102 is within the scope of the present disclosure.

Lower portion 105 comprises a middle portion 104 and a base 106 positioned at the opposite end of socket 100 from conical cup 102. In various embodiments, lower portion 105 is unitary and made from a single material, such that middle portion 104 and base 106 are unitary and integral. In other embodiments, the components of lower portion 105, namely middle portion 104 and base 106, are separate and distinct from each other.

In various embodiments, middle portion 104 of lower portion 105 is coupled to conical cup 102 and base 106. Further, a prosthetic device, such as a prosthetic arm or leg, is attached and secured to base 106.

In various embodiments, lower portion 105 (which is coupled to conical cup 102) can comprise, for example, a polymeric material. In various embodiments, lower portion 105 comprises the same polymeric material as conical cup 102. In other embodiments, lower portion 105 comprises a different polymeric material than conical cup 102. For example, lower portion 105 can comprise a polymeric material having a second pliability that is less than the pliability of the polymeric material of conical cup 102. However, lower portion 105 can comprise any suitable polymeric material.

Similar to conical cup 102, lower portion 105 can comprise a polymeric material having one or more additives which are added to the polymeric material to impart one or more desired physical and/or chemical properties to the polymeric material. For example, the polymeric material of lower portion 105 may comprise one or more of fiberglass, carbon fiber, aramid fiber, glass beads, carbon nanotubes, or other additives. Any additive that imparts or improves a desired physical or chemical property of the polymeric material of lower portion 105 is within the scope of the present disclosure.

In various embodiments, lower portion 105 is injection molded form a polymeric material. For example, lower portion 105 can be injection molded from the same material as conical cup 102. Further, lower portion 105 can be injection molded with conical cup 102, creating a unitary polymeric socket 100. Stated another way, polymeric socket 100 can comprise a "one piece" design where the conical cup 102 and lower portion 105 (including its components; middle portion 104 and base 106) are all made jointly and simultaneously, and are essentially a single piece.

In other embodiments, lower portion 105 (including one or both of middle portion 104 and base 106) can be injection molded separately from conical cup 102 and secured to conical cup 102 via including mechanical methods, adhesives, or any other any suitable manner of coupling the two components. In other embodiments, lower portion 105 can be over-molded, such that it is formed in contact with conical cup 102 after injection molding of conical cup 102 utilizing both parts.

In various embodiments, base 106 is injection molded from a polymeric material, which may or may not comprise the same polymeric material from which conical cup 102 and/or lower portion 105 are formed.

Figure 3:
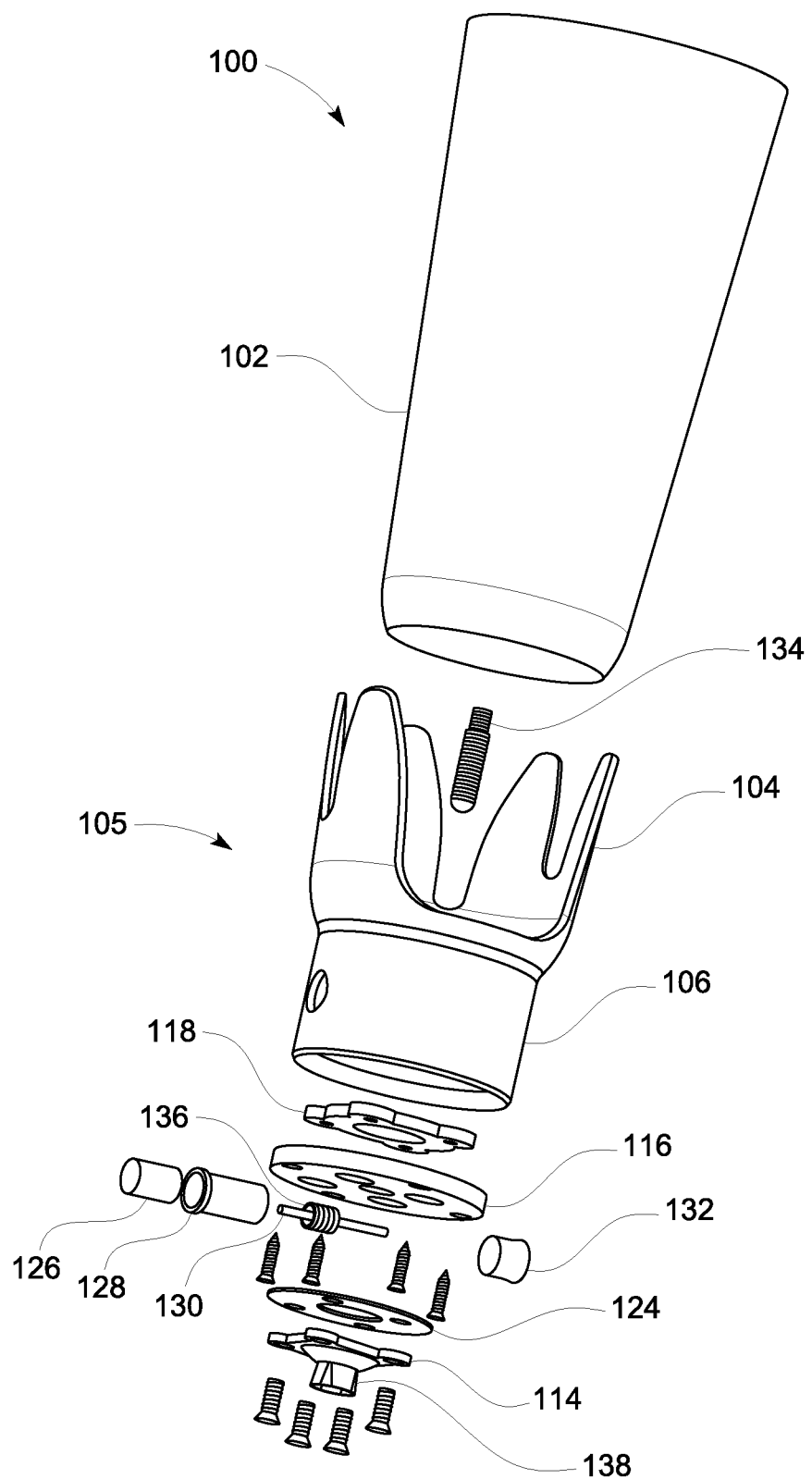
FIG. 3 illustrates an exploded view of the prosthetic limb socket of FIGS. 1 and 2 in accordance with the present disclosure.
Figure 6:
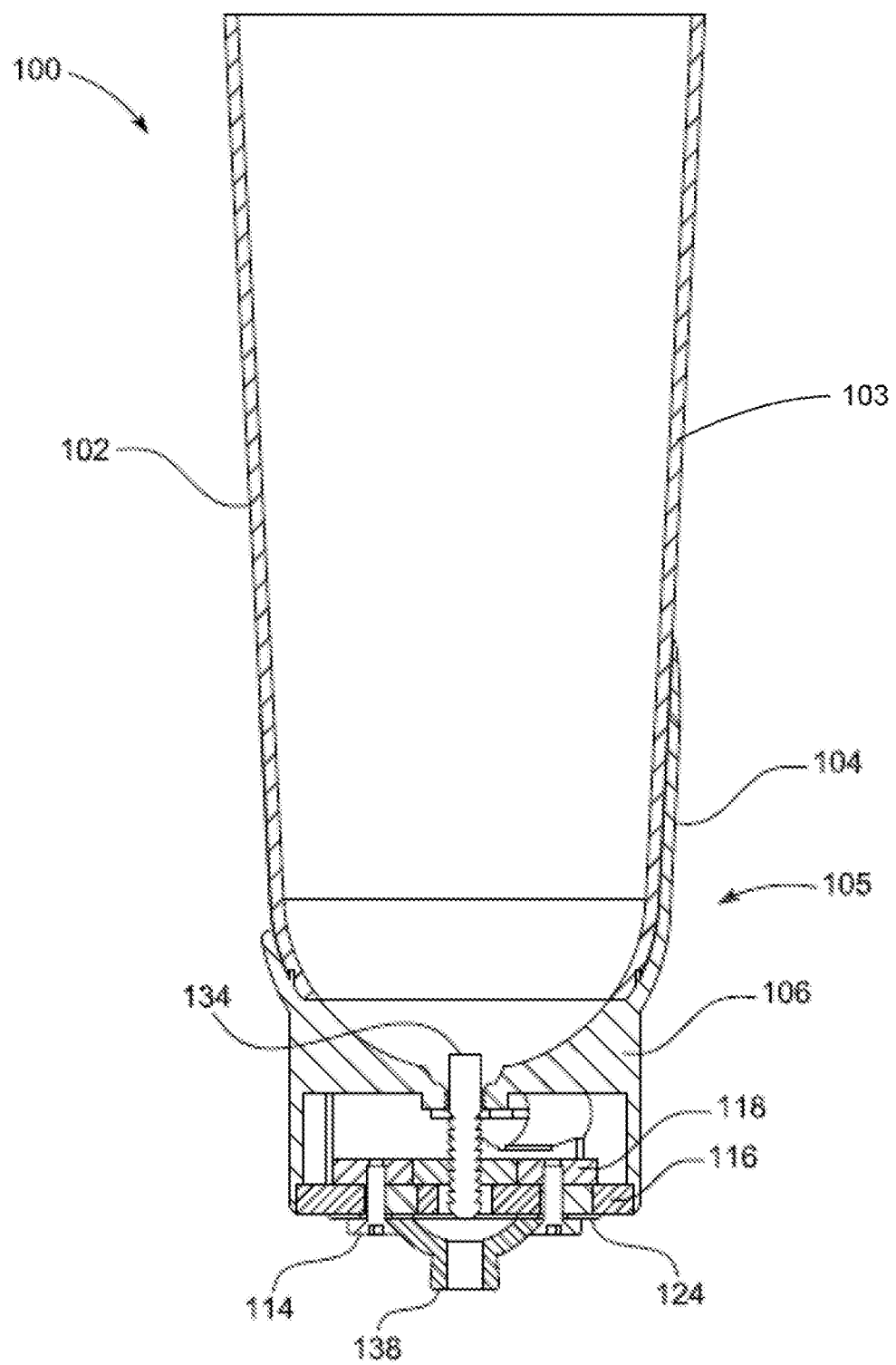
FIG. 6 illustrates a cut-away side view of the prosthetic limb socket of FIGS. 1-5 in accordance with the present disclosure.
Figure 7:
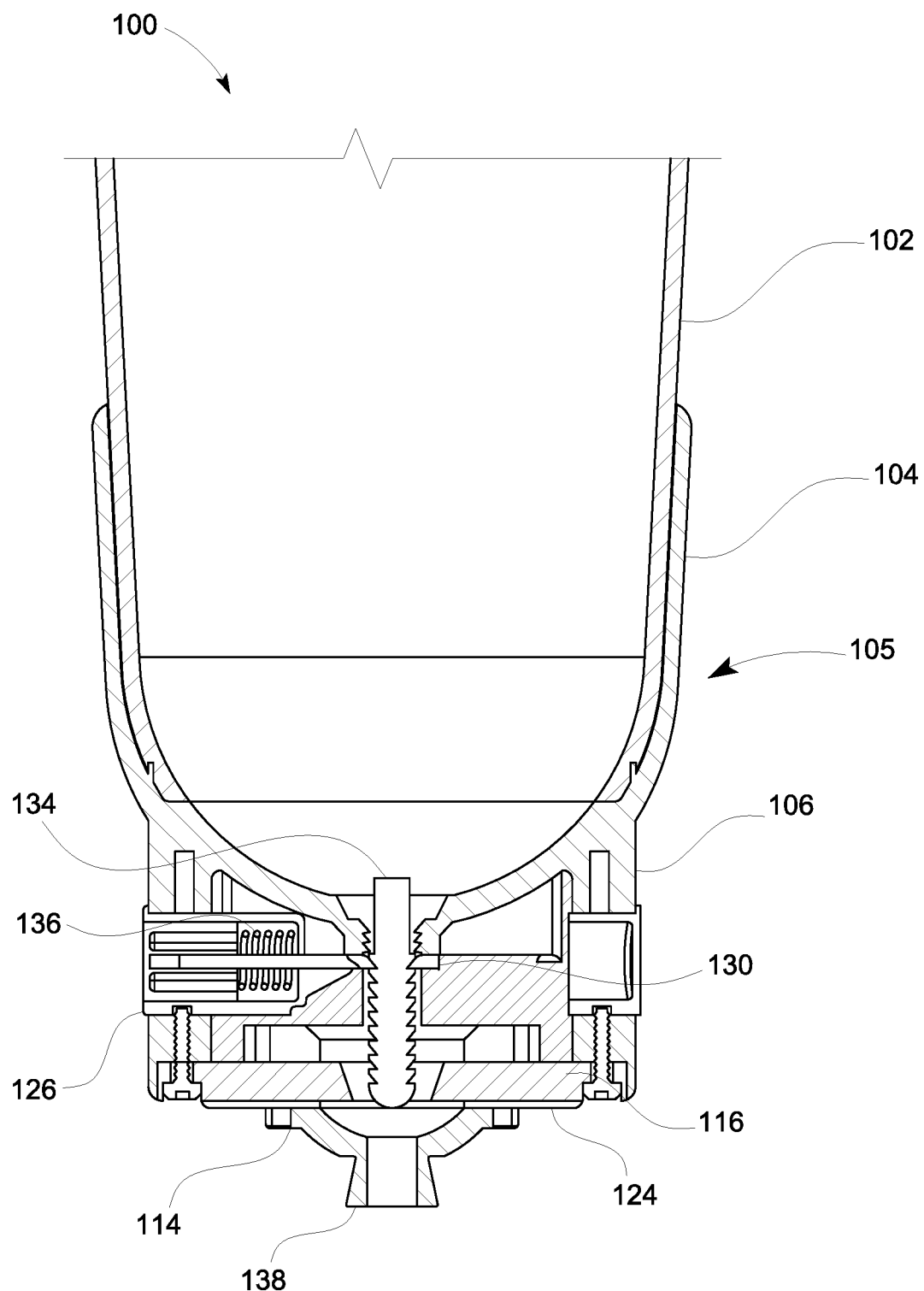
FIG. 7 illustrates a side cut-away view of another prosthetic limb socket in accordance with the present disclosure.

With initial reference to FIGS. 3, 6, and 7, socket 100 comprises means to secure a prosthetic limb to lower portion 105, and more specifically, to base 106 of socket 100. In various embodiments, socket 100 comprises a base plate 116 coupled to a locking plate 118. For example, base plate 116 can be secured to locking plate 118 by one or more threaded screws.

In various embodiments, an attachment member 114 can be secured to base plate 116. Attachment member 114 can comprise, for example, a receptacle 138 which engages with and secures a prosthetic limb to socket 100. For example, receptacle 138 can comprise one of a ball or socket, which is configured to engage with a corresponding element of a prosthetic limb to secure the limb to socket 100 in a "ball and socket" arrangement. Although described with reference to a specific physical member, any physical configuration of base plate 116 and attachment member 114 capable of coupling a prosthetic limb to socket 100 is within the scope of the present disclosure.

Figure 4:
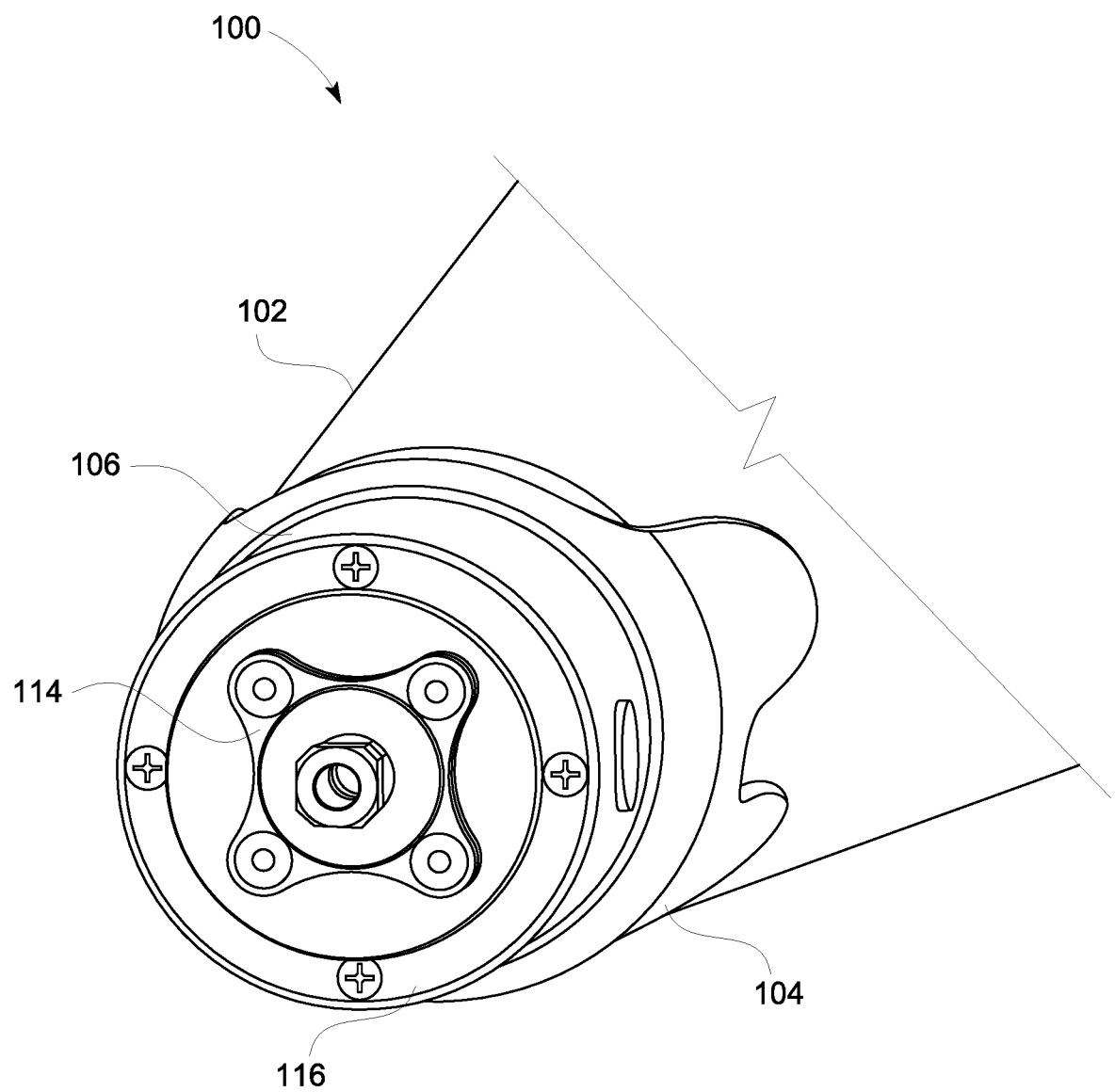
FIG. 4 illustrates another perspective view of the prosthetic limb socket of FIGS. 1-3 in accordance with the present disclosure.
Figure 5:
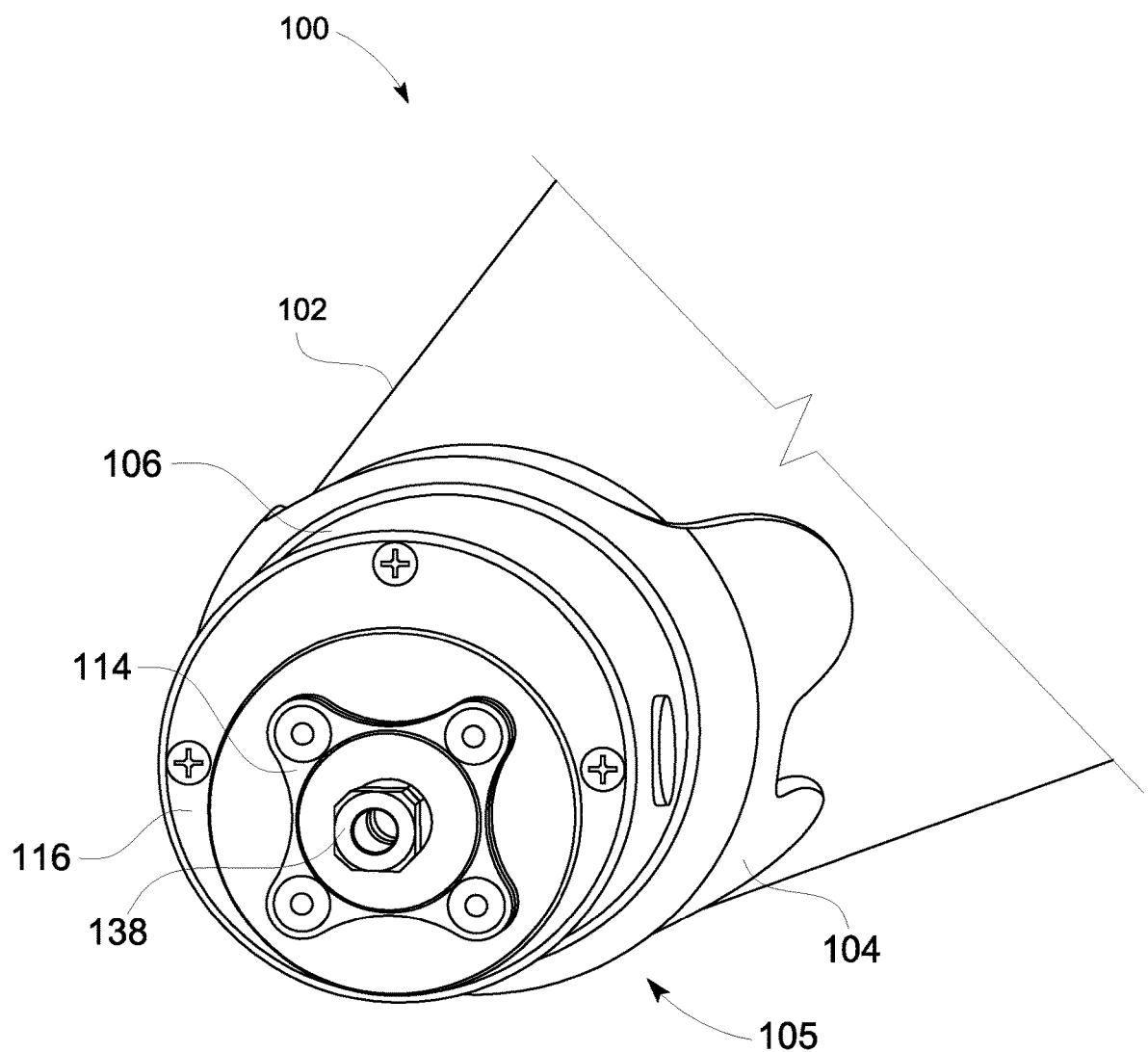
FIG. 5 illustrates a perspective view of the prosthetic limb socket of FIGS. 1-4 in an offset configuration in accordance with the present disclosure.

In various embodiments, locking plate 118 can slide along base plate 116. For example, by loosening the screws that secure base plate 116 to locking plate 118, locking plate 118 can slide and change orientation with regards to base plate 116, allowing attachment member 114 to change orientation relative to socket 100. With initial reference to FIG. 4, a socket 100 having a normally-oriented attachment member 114 is illustrated. In this case, "normally-oriented" means perpendicular to socket 100. Stated another way, base plate 116 and locking plate 118 are oriented planar to one another, such that attachment member 114 is perpendicular to socket 100. With initial reference to FIG. 5, a socket 100 having an offset attachment member 114 is illustrated. Stated another way, base plate 116 and locking plate 118 are oriented offset (or non-planer) to one another, such that attachment member 114 is not perpendicular to (i.e., is offset from) socket 100. Such adjustment allows for the prosthetic limb coupled to attachment member 114 to be oriented properly relative to the residual limb of the patient.

Socket 100 can further comprise, for example, a cover 124 positioned proximal base 106. For example, cover 124 can be positioned at or near the bottom of base 106 and can prevent dirt or other contaminants from entering base 106 and socket 100.

In various embodiments, socket 100 can further comprise a typical locking pin 134 that couples the liner to socket 100. In various embodiments, locking pin 134 is secured to socket 100 by a pin plate 130. For example, pin plate 130 can move laterally with regards to locking pin 134 by, for example, button 126, which engages and disengages pin plate 130 from locking pin 134. Locking pin 134 may, for example, comprise ridges that engage with pin plate 130, such that as locking pin 134 of the liner is inserted into the locking mechanism of base 106, it click locks incrementally, securing the liner into base 106 and socket 100. In various embodiments, button 126 is housed within button housing 128. Further, a housing cover 132 may be positioned on a side of button housing 128 opposite button 126. Pin plate 130 can further comprise a spring 136.

Figure 8:
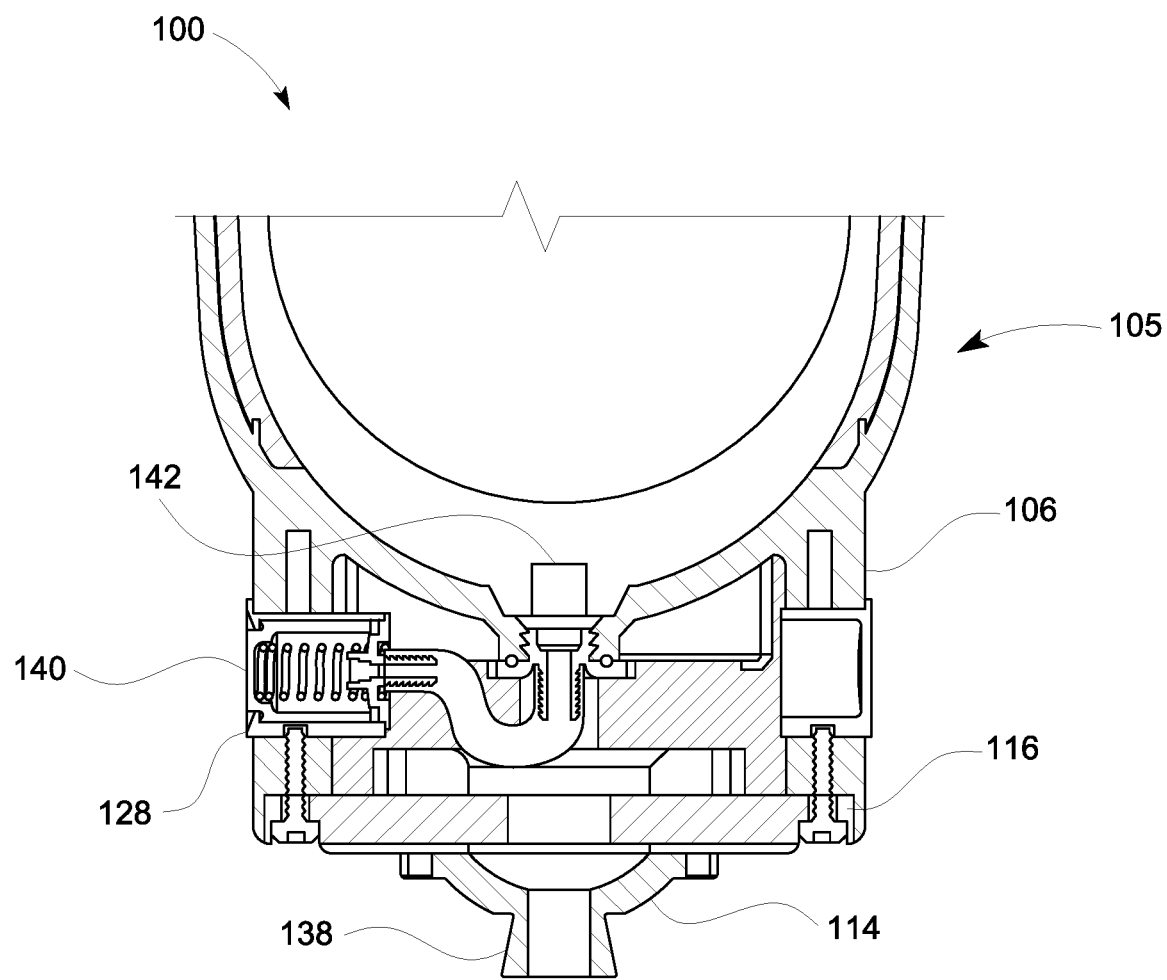
FIG. 8 illustrates a side cut-away view of yet another prosthetic limb socket in accordance with the present disclosure.
Figure 9:
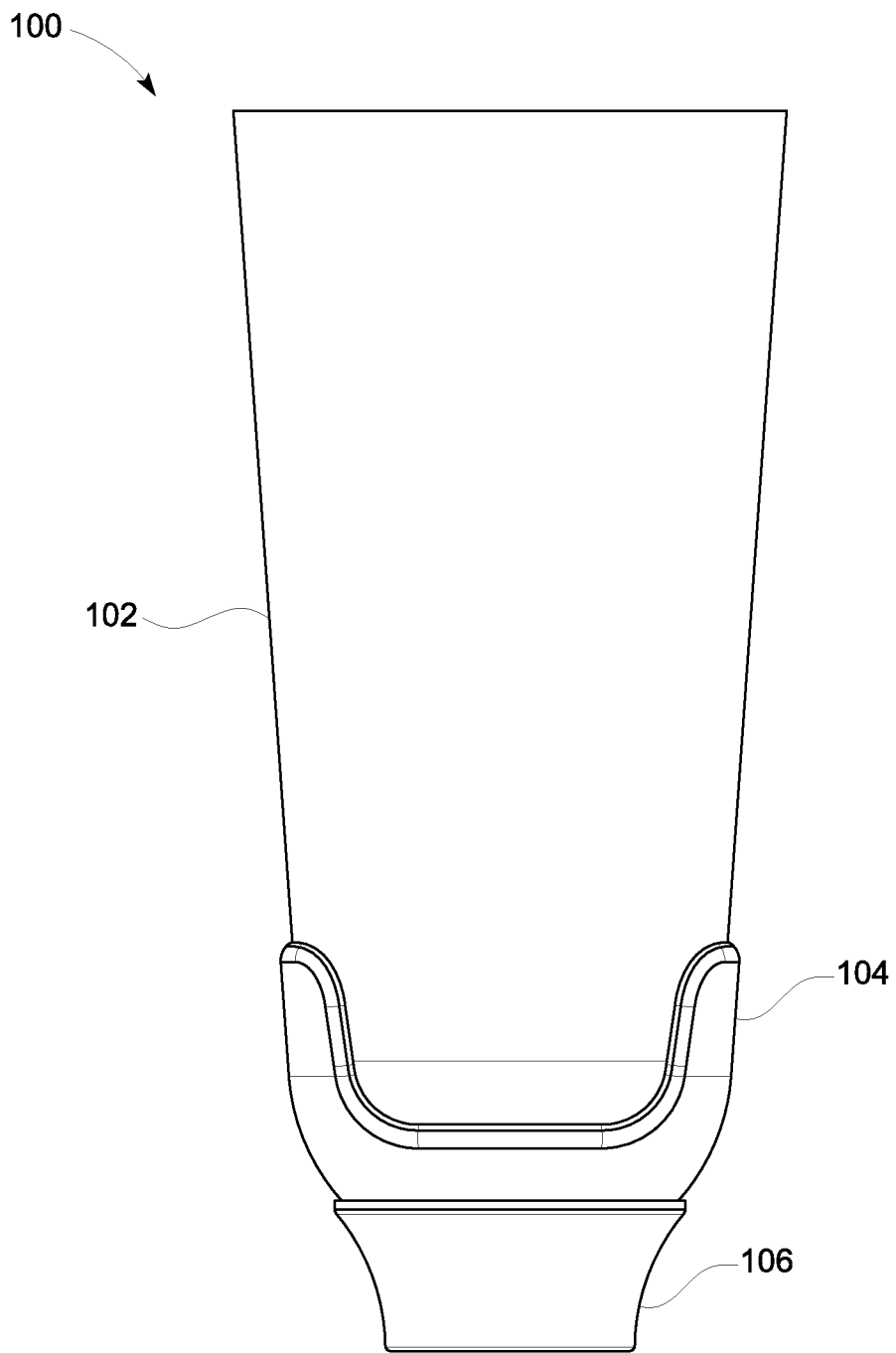
FIG. 9 illustrates a side view of a prosthetic limb socket in accordance with the present disclosure.
Figure 10:
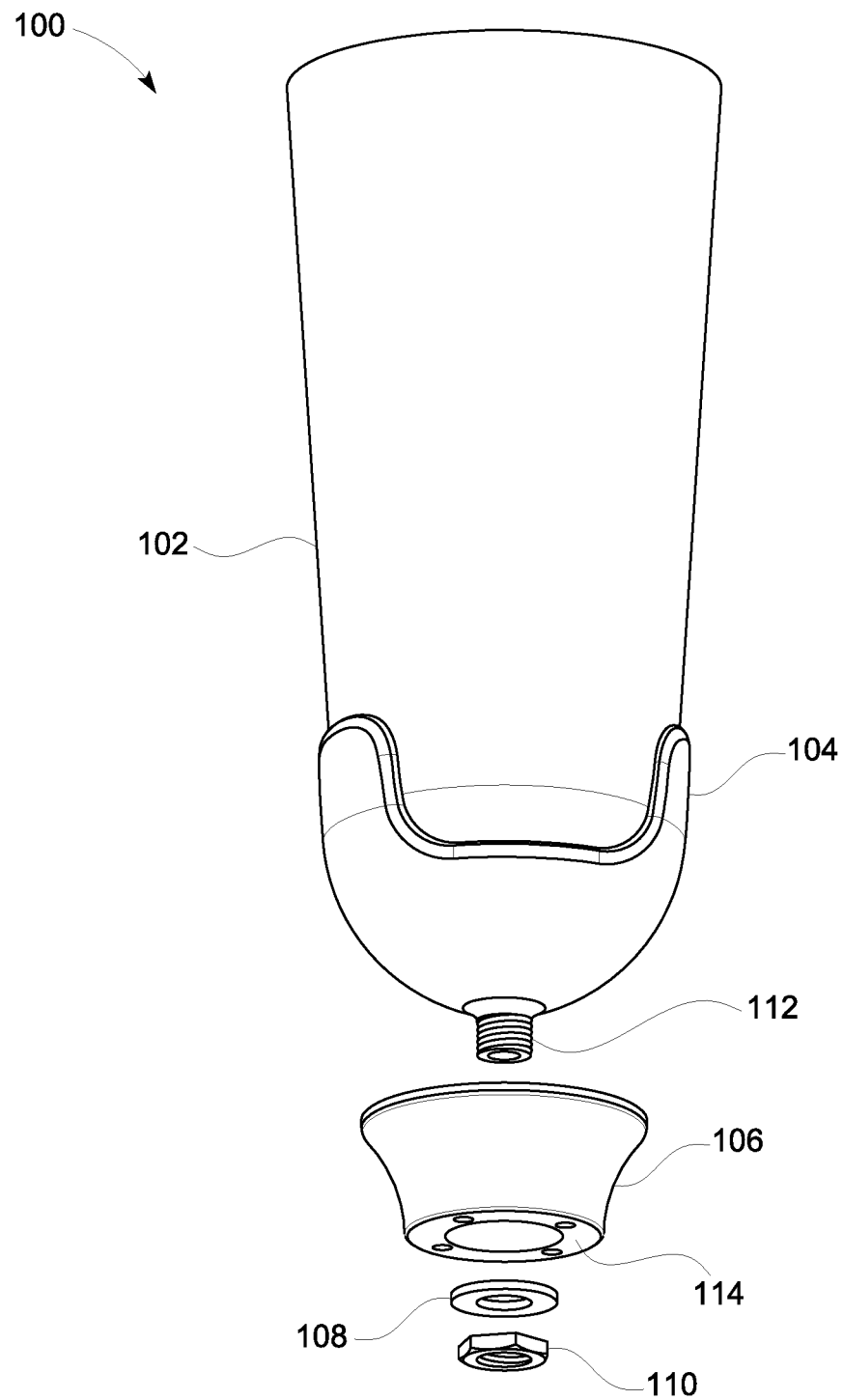
FIG. 10 illustrates an exploded view of the prosthetic limb socket of FIG. 9, in accordance with the present disclosure.
Figure 11:
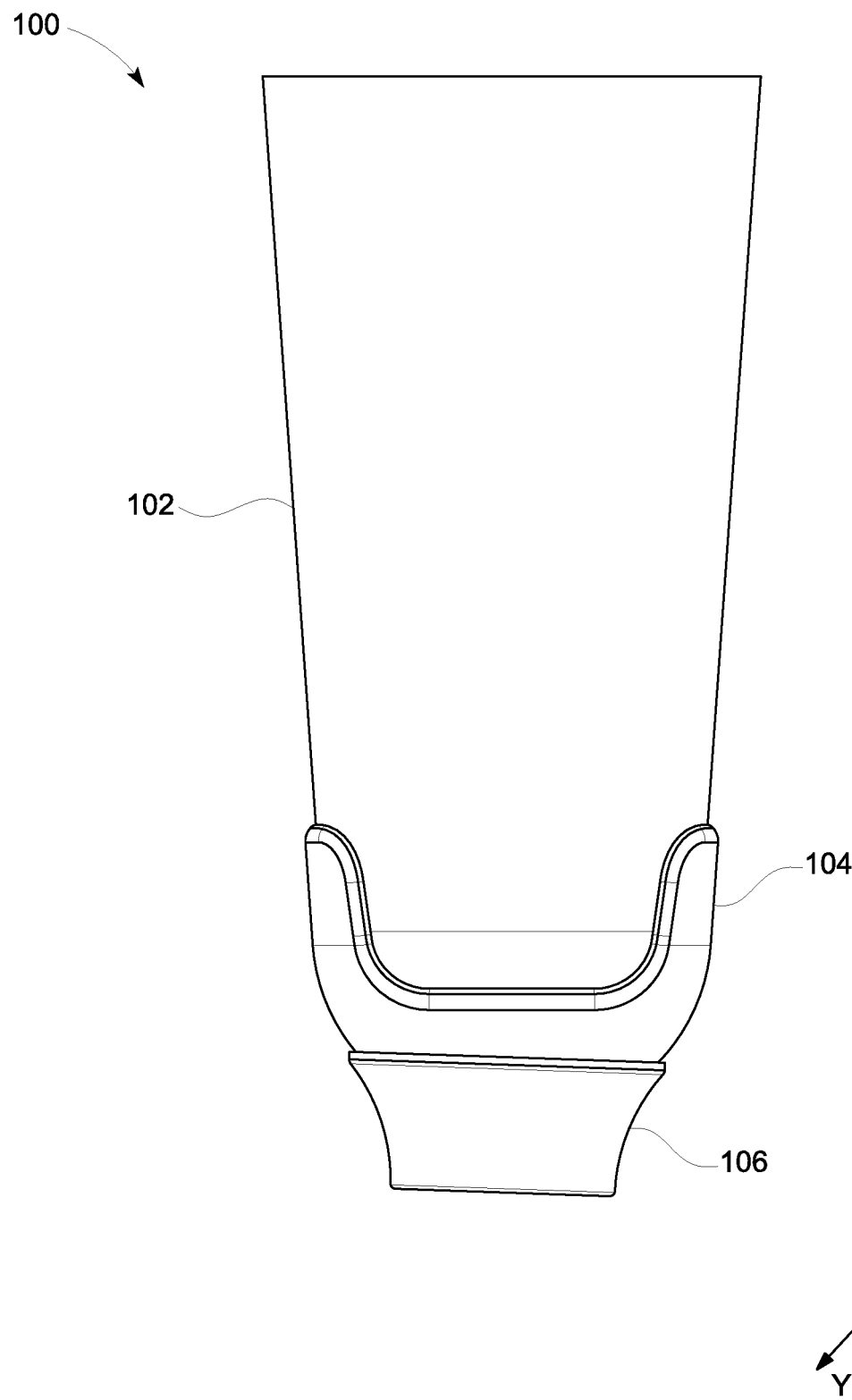
FIG. 11 illustrates a side view of the prosthetic limb socket of FIGS. 9 and 10 in an offset configuration in accordance with the present disclosure.
Figure 12:
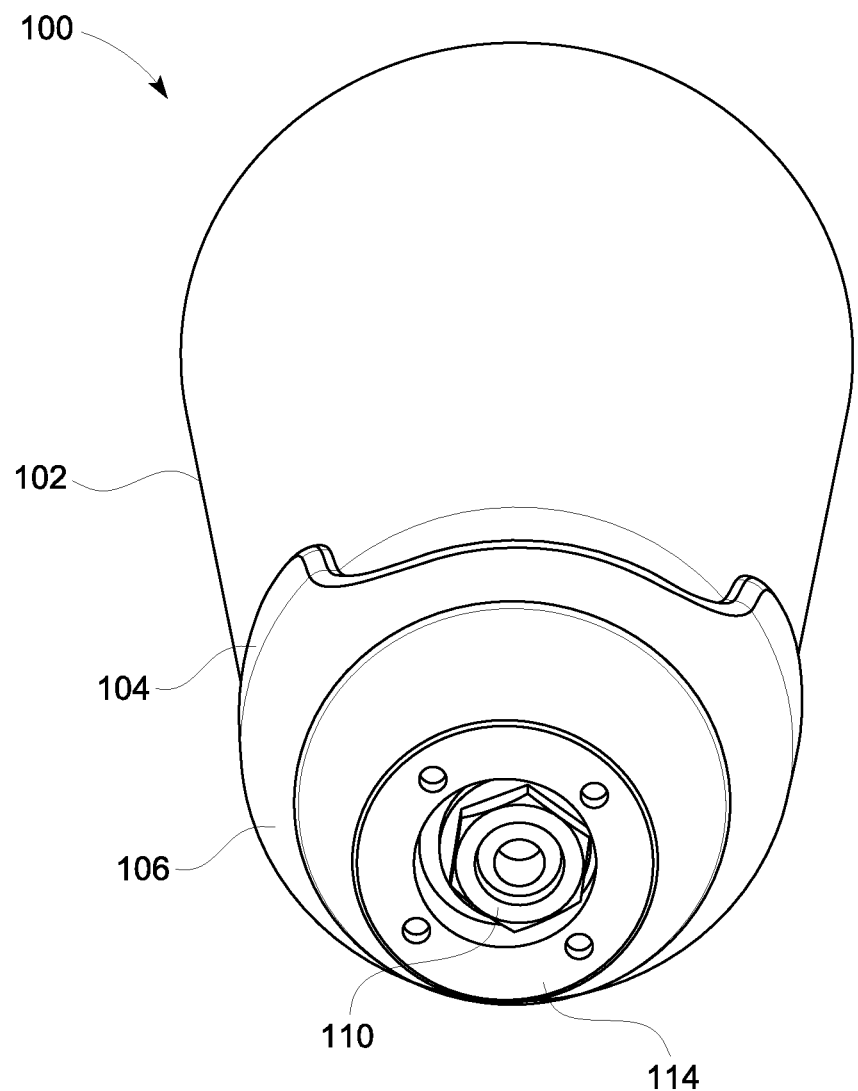
FIG. 12 illustrates a perspective view of the prosthetic limb socket of FIGS. 9 and 10 in an offset configuration in accordance with the present disclosure.
Figure 13:
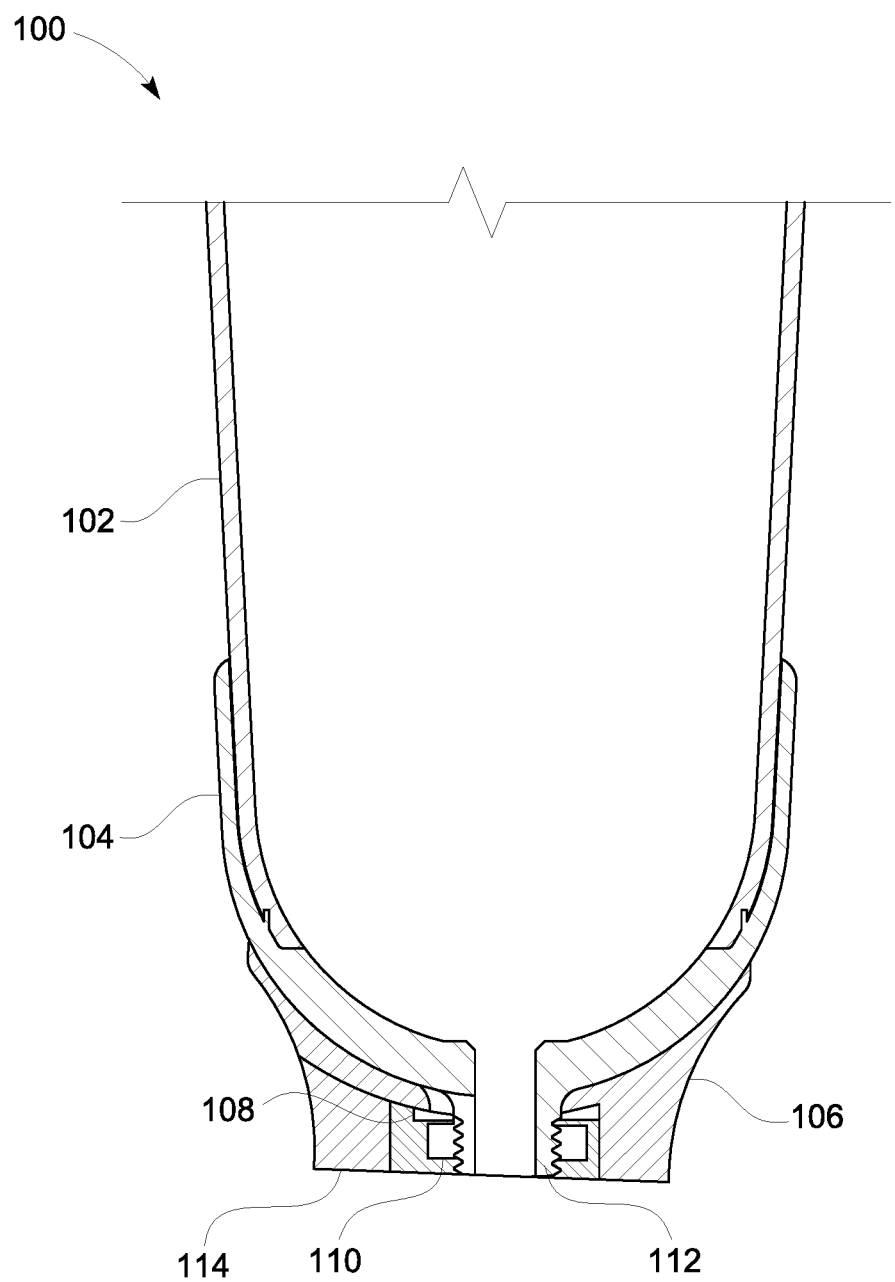
FIG. 13 illustrates a side cut-away view of the prosthetic limb socket of FIGS. 9 and 10 in an offset configuration in accordance with the present disclosure.

With initial reference to FIG. 8, another embodiment of socket 100 is illustrated. For example, socket 100 can comprise a vacuum port 140 configured to apply vacuum through vacuum outlet 142 against a gel liner attached to a patient. Vacuum port 140 can be positioned in housing 128 (previously referred to as button housing 128 in connection with other embodiments), and can be quickly and easily accessed by the patient and prosthetists to apply or reduce suction to socket 100, allowing for securement or removal of socket 100 from the liner. Although described with reference to specific physical configurations, any manner of coupling socket 100 to a prosthetic liner is within the scope of the present disclosure.

Numerous methods of securing socket 100 to a liner (and thus the residual limb) can be utilized. For example, the following methods are also within the scope of the present disclosure;

The liner has a soft ring shaped ridge near the bottom (not shown) that creates an air tight seal to the interior of socket 100 and conical cup 102. As the residual limb is pushed into conical cup 102, the air is expelled through a valve at base 106. The liner is tightly held to socket 100 by suction. To remove socket 100 form the residual limb, a button is depressed allowing air into socket 100 and breaking the suction;

A sleeve (not shown) is placed over the top of conical cup 102 of socket 100, extending upwards over at least a portion of the residual limb. The sleeve fits tight to form an air tight seal between socket 100 and the skin of the residual limb. This creates suction holding the liner to socket 100. The sleeve is rolled down the residual limb and socket 100 to break the seal, allowing socket 100 to be removed; and A sleeve can be used to seal socket 100 to the residual limb in conjunction with a vacuum pump that creates negative pressure, sucking the liner into conical cup 102 of socket 100. These pumps can be hand activated, activated by walking, or by using an electro-mechanical pump to create suction.

Socket 100 can further comprise, for example, a coupling member to couple and secure socket 100 to a liner of a residual limb. In various embodiments, the coupling member attaches base 106 to the liner. Such coupling members can comprise, for example, a clip (such as a spring clip) that engages a locking post of the gel liner, an air tight button seal to allow air to escape, be sealed, and be released for use with a suction socket retention system, and/or a hose attachment that couples to a vacuum source that applies negative pressure between base 106 and the gel liner. Although described with reference to specific mechanical member, any manner of coupling socket 100 with a prosthetic limb is within the scope of the present disclosure.

With initial reference to FIGS. 9-13, in various embodiments, base 106 is secured to middle portion 104 via a fastening member 112. For example, a fastening member 112 can be formed into or otherwise secured to a bottom surface of middle portion 104 or conical cup 102. In various embodiments, fastening member 112 passes through a portion of base 106 and is secured by a corresponding member 110, holding base 106 in position relative to middle portion 104. For example, fastening member 112 can comprise a threaded portion protruding from middle portion 104 into base 106. A washer 108 and nut 110 are coupled to fastening member 112, which secures base 106 to middle portion 104. Although described with reference to specific arrangements, any manner of coupling base 106 to middle portion 104 or conical cup 102 is within the scope of the present disclosure.

In various embodiments, an attachment member 114 can be secured to base 106 by fastening member 112 and corresponding member 110. For example, attachment member 114 can be positioned along fastening member 112 (e.g., a threaded portion) and secured via member 110 (e.g., a nut). Although described with reference to the various drawing figures and specific embodiments, any manner of securing attachment member 114 to socket 100 is with the scope of the present disclosure.

For example, base 106 can comprise a mechanical attachment member 114 to couple a component of the prosthetic arm or leg to socket 100. In various embodiments, attachment member 114 comprises a baseplate which attaches to the prosthetic limb by, for example, screws.

In various embodiments, attachment member 114 is adjustable in one or more planes or directions. With reference to FIGS. 6-8, attachment member 114 of base 106 allows for positional adjustment of socket 100 and the prosthetic limb with respect to each other. For example, the prosthetic limb may be offset horizontally from a center axis of socket 100 in order to properly orient and position the socket 100 and the prosthetic limb for optimal use, gait, and/or balance. In various embodiments, attachment member 114 comprises a baseplate which attaches to the prosthetic limb in a manner that allows for angular adjustment between base 106 and the prosthetic limb. For example, the adjustment member 114 may be bolted to the prosthetic limb, and loosening the bolts can allow for the base plate to be slid and adjusted in a planar horizontal manner to offset the prosthetic limb as desired. Tightening the bolts locks base 106 and the prosthetic limb in position relative to one another.

In various embodiments, socket 100 further comprises an insert layer. In such embodiments, the insert layer can be positioned within conical cup 102, and comprises a material that causes conical cup 102 to draw tight circumferentially over the residual limb as it is heated and formed around the limb. In various embodiments, an insert layer can comprise one or more of a knit fabric, a mesh, and/or a thin sheet or perforated material of stretch rubber, polyurethane, estane, spandex, or long chain polymer. Although described with reference to specific materials, an insert layer can comprise any material suitable for circumferentially tightening a portion of socket 100 (such as conical cup 102) when heated.

Further, an insert layer can comprise a protruding portion that extends upward from the opening of conical cup 102. In such embodiments, for example, the protruding portion may comprise one or more handles, which can be used to help pull socket 100 onto the residual limb during forming.

In various embodiments, socket 100 can further comprise an outer layer 103 that surrounds at least a portion of socket 100. The outer layer 103 may provide a durable, smooth outer surface of socket 100, and may be printable and/or textured for cosmetic purposes. For example, the outer layer 103 can be co-molded or adhered to an outer surface of socket 100 (such as, for example, an outer surface of conical cup 102). In various embodiments, the outer layer 103 comprises a sheet material, such as vinyl, PVC or other plastic that becomes pliable and stretchable at between about 160° F. and about 302° F. (70° C. and about 150° C., and further, between about 225° F. and 275° F. (107° C. to 135° C.). Further, the outer layer 103 can have a thickness, for example, between about 0.0050" and about 0.025" (0.127 mm and 0.3157 mm).

In various embodiments, methods of forming sockets 100 to residual limbs comprise selecting the appropriate socket size. For example, conical cup 102 of socket 100 can comprise a circumference that is smaller than the circumference of the residual limb. In such embodiments, when socket 100 and conical cup 102 are heated, the material of socket 100 becomes sufficiently pliable and stretchable to allow conical cup 102 to be stretched over the residual limb.

As socket 100 cools, conical cup 102 contracts to its pre-heated circumference, providing a circumferentially tight fit to the residual limb.

Socket 100 and conical cup 102 can be sized using a set of pre-sized plastic or foam cups that are used to measure the residual limb having a liner in place. For example, the different sized cups can include a label with the corresponding suggested socket size that is smaller in circumference than the sizing cup, so as to achieve the correct percentage of reduction in circumference of socket 100 and conical cup 102 after heating, resulting in a proper tight fit.

In various embodiments, spaces or voids can be created within socket 100 to correspond with sensitive portions of the residual limb. For example, padding such as foam pieces, tapered gel pads, cotton wadding or other forms can be applied directly to the skin and placed under the gel liner worn by the amputee, creating extra space within socket 100 during the heat forming process. The padding can be removed after cooling and hardening of socket 100.

Figure 14:
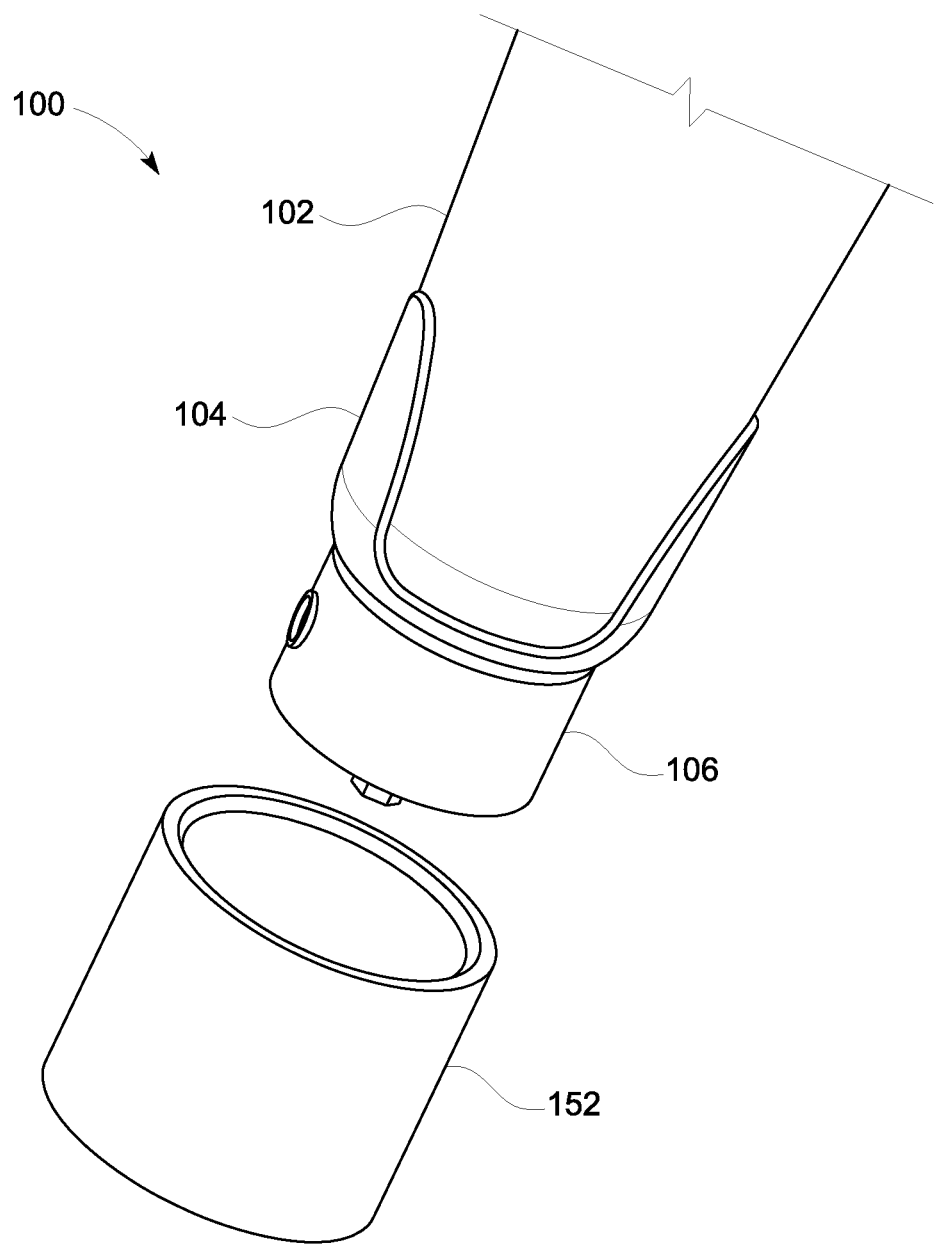
FIG. 14 illustrates a perspective view of a prosthetic limb socket and an insulating cover in accordance with the present disclosure.

Sockets 100 in accordance with the present disclosure are fitted to residual limbs by heating a portion of socket 100 to a predetermined temperature, allowing the portion of socket 100 to be plastically deformed to conform to the residual limb. In various embodiments, socket 100 is differentially heated so that conical cup 102 is heated to a temperature of between 225° F. and 275° F. (107° C. to 135° C.), while base 106 remains at or near room temperature. For example, with reference to FIG. 14, an insulating cup 152 may be fitted to a portion of lower section 105 (for example, base 106) to reduce heat transferred into the portion of lower section 105 and preventing any change in shape of the portion. Suitable insulating cups 152 can comprise, for example, molded foam, fabric insulative batting, silicone, or any material capable of adequately insulating a portion of lower section 105, and capable of withstanding repeated heating cycles without deteriorating. After sufficiently heating socket 100, insulating cup 152 may be removed from socket 100.

In various embodiments, a method for applying socket 100 can further comprise applying an insulating cover (not shown) over the outer surface of a portion of socket 100. For example, an insulating cover can be applied before or after heating, and can apply circumferential compression to the heated section of socket 100 (such as, for example, conical cup 102). The insulating cover may prevent heat loss from socket 100, extending the working time of socket 100 and allowing for more time to fit socket 100 to a residual limb.

For example, the insulating cover may comprise a tubular or cup shaped cover comprising a stretch insulating material such as neoprene foam with a stretch fabric covering such as wetsuit material, closed-cell foam, knit stretch fabric, spandex fabric and the like. Further, the insulating cover can comprise strapping applied vertically and extending above the top of the cover to provide handles for pulling the socket onto the residual limb. Once socket 100 is properly installed on the residual limb, the insulating cover can be removed from socket 100.

Methods for applying socket 100 can further comprise applying an outer sleeve around a portion of socket 100. For example, a woven or knit outer sleeve can be fitted around a portion of socket 100 before or after heating. In various embodiments, the outer sleeve can apply pressure to socket 100 such that the circumference of a portion of socket 100 (such as, for example, conical cup 102) is reduced as the outer sleeve is stretched vertically. In such embodiments, the outer sleeve operates similarly to a Chinese finger trap. The outer sleeve can comprise a material woven in a diagonal pattern.

Further, the outer sleeve can being suspended above socket 100 by a framework. For example, the framework can comprise a hoop from which the outer sleeve is suspended, in a configuration similar to a basketball hoop and net. The opposite (e.g., bottom) end of the outer sleeve can comprise a rigid ring that fits over the base 106, thereby locking it to outer sleeve. In such embodiments, after heating socket 100 to the working temperature, the residual limb is inserted into socket 100, and the downward pressure applied by the residual limb vertically extends the outer sleeve, causing it to circumferentially compress pliable socket 100 around the residual limb.

In the present disclosure, the words "a" or "an" are to be taken to include both the singular and the plural. Conversely, any reference to plural items shall include, where appropriate, the singular.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

We claim:

1. A prosthetic limb socket, comprising:
   a conical cup comprising:
      an opening for insertion of a residual limb,
      an end opposite the opening for enclosing the residual limb,
      the conical cup configured to be stretched circumferentially around the residual limb,
      the conical cup being pliable at temperature between 70° C. and 150° C.,
      the conical cup, when heated to the temperature, having a working time of between five minutes and 15 minutes, allowing the conical cup to be heat formed directly onto the residual limb before hardening; and
   a lower portion coupled to the end of the conical cup, the lower portion comprising:
      a middle portion co-molded to and enclosing the end of the conical cup, the middle portion designed to support the prosthetic limb socket during heat forming, and
      a base secured to the middle portion through a fastening member that is attached on a bottom surface of the middle portion, the base having a cylindrical shape and comprising:
         a base plate positioned at a bottom of the base, the base plate configured to couple the prosthetic limb socket to a prosthetic limb,
         wherein the middle portion is designed to be less pliable at the temperature than the conical cup, and the base is designed to remain rigid at the temperature.

2. The prosthetic limb socket of claim 1, wherein the conical cup and the lower portion are unitary.

3. The prosthetic limb socket of claim 1, wherein the lower portion is over-molded to the conical cup.

4. The prosthetic limb socket of claim 1, wherein the conical cup is composed of a thermoplastic polymer that comprises at least one additive from the group of fiberglass, carbon fiber, aramid fiber, glass beads, and carbon nanotubes.

5. The prosthetic limb socket of claim 1, further comprising an insert layer comprising one of a rubber, a polyurethane, an estane, spandex, a long chain polymer.

6. The prosthetic limb socket of claim 5, wherein the insert layer is an insert molded into the conical cup, and wherein the insert layer causes the conical cup to draw tight circumferentially over the residual limb as it is applied and formed.

7. The prosthetic limb socket of claim 1, further comprising an outer layer surrounding at least a portion of the conical cup.

8. The prosthetic limb socket of claim 7, wherein the outer layer is co-molded or adhered to an external surface of the socket.

9. The prosthetic limb socket of claim 1, further comprising an insulating layer configured to be attached to the residual limb and secured within the conical cup.

10. The prosthetic limb socket of claim 1, wherein an attachment member having a receptacle is coupled to the base.

11. The prosthetic limb socket of claim 10, further comprising an insulating cover configured to prevent heating of the base during heating of the conical cup.

12. The prosthetic limb socket of claim 1, wherein the conical cup comprises a circumference that is configured to be smaller than a circumference of the residual limb.

13. A method for securing the prosthetic limb socket of claim 1 to the residual limb comprising:
heating the prosthetic limb socket to a temperature between 70° C. and 150° C.

14. The method of claim 13, further comprising:
stretching the conical cup of the prosthetic limb socket over the residual limb.

15. The method of claim 14, further comprising:
placing a piece of at least one of a foam, gel, and fabric within a liner placed over the residual limb for creating a corresponding void during stretching of the conical cup over the residual limb.

16. The method of claim 13, wherein the method further comprises positioning an insulating cover over a portion of the base, and wherein the insulating cover prevents heating of the base during the heating of the conical cup.

17. The method of claim 13, wherein, before heating the prosthetic limb socket, the conical cup comprises a circumference that is smaller than a circumference of the residual limb.

18. The method of claim 13, further comprising:
sizing the conical cup of the prosthetic limb socket by identifying a circumference of the residual limb using a sizing aid; and
calculating a circumference of the conical cup using a reduction factor associated with the sizing aid.

19. The method of claim 13, further comprising:
applying an outer sleeve around a portion of the conical cup, wherein the outer sleeve reduces a circumference of the conical cup as the outer sleeve is stretched vertically.

20. The method of claim 19, further comprising:
after heating the prosthetic limb socket, inserting the residual limb into the prosthetic limb socket and applying downward weight, thereby extending the outer sleeve and causing it to circumferentially compress a portion of the prosthetic limb socket onto the residual limb.

* * * * *